US006451311B2

(12) United States Patent
Althaus et al.

(10) Patent No.: US 6,451,311 B2
(45) Date of Patent: Sep. 17, 2002

(54) ANTI-PROCALCITONIN ANTIBODIES AND THE PREPARATION AND USE THEREOF

(75) Inventors: Harald Althaus, Wetter; Götz Walter, Münchhausen, both of (DE)

(73) Assignee: Dade Behring Marburg GmbH, Marburg (DE)

( * ) Notice: Subject to any disclaimer, the term of this patent is extended or adjusted under 35 U.S.C. 154(b) by 0 days.

(21) Appl. No.: 09/742,375

(22) Filed: Dec. 22, 2000

(30) Foreign Application Priority Data

| Dec. 22, 1999 | (DE) | 199 62 417 |
| Apr. 3, 2000 | (DE) | 100 16 277 |
| Aug. 22, 2000 | (DE) | 100 41 215 |

(51) Int. Cl.$^7$ ...... A61K 49/00; A61K 39/395; C12P 21/04; C07K 16/00; C07K 17/00; C12N 1/20; C12N 15/82; C12N 15/86

(52) U.S. Cl. ...... 424/158.1; 424/9.1; 424/141.1; 424/142.1; 424/145.1; 424/178.1; 530/387.1; 530/388.1; 530/388.15; 530/388.24; 530/391.1; 530/391.3; 530/391.9; 435/70.21; 435/252.8; 435/326; 435/331; 435/346; 435/366; 435/410; 435/455; 435/810

(58) Field of Search ...... 530/387.1, 388.1, 530/388.15, 388.24, 391.1, 391.3, 391.9; 424/141.1, 142.1, 145.1, 158.1, 178.1, 9.1; 435/70.21; 455/810, 366, 252.8, 410, 331, 346, 326

(56) References Cited

U.S. PATENT DOCUMENTS

| 3,996,345 A | | 12/1976 | Ullman et al. |
| 5,340,716 A | | 8/1994 | Ullman et al. |
| 5,545,834 A | | 8/1996 | Singh et al. |
| 5,858,682 A | * | 1/1999 | Gruenwald et al. |
| 5,993,811 A | * | 11/1999 | Becker et al. |

FOREIGN PATENT DOCUMENTS

| DE | 198 47 690 A1 | 4/2000 |
| DE | 199 03 336 A1 | 8/2000 |
| EP | 0 080 614 A2 | 11/1982 |
| EP | 0 227 054 B1 | 12/1986 |
| EP | 0 246 446 B1 | 4/1987 |
| EP | 0 411 945 A2 | 8/1990 |
| EP | 0 515 194 A2 | 5/1992 |
| EP | 0 656 121 B1 | 8/1993 |
| WO | WO 98/33524 | 1/1988 |
| WO | WO 94 04927 A | 3/1994 |
| WO | WO 95/06877 | 3/1995 |
| WO | WO 95/25172 | 9/1995 |
| WO | WO 98 33524 A | 8/1998 |

OTHER PUBLICATIONS

P. Ghillani et al., "Monoclonal Antipeptide Antibodies As Tools To Dissect Closely Related Gene Products: A Model Using Peptides Encoded By The Calcitonin Gene," Journal of Immunology, vol. 141/9, pp. 3156–3163 (1988).

J.M. Le Moullec et al., "The complete sequence of human preprocalcitonin," FEBS 1198, vol. 167, No. 1, Feb. 1984, pp. 93–97.

J. Michael Conlon et al., "Structural characterization of a high–molecular–mass form of calcitonin [procalcitonin–(60–116)–peptide] and its corresponding N–terminal flanking peptide [procalcitonin–(1,57)–peptide] in a human medullary thyroid carcinoma," Biochem, vol. 256, 1988, pp. 245–250.

Pascale P. Ghillani et al., "Identification and Measurement of Calcitonin Precursors in Serum of Patients with Malignant Diseases," Cancer Research, vol. 49, Dec. 1, 1989, pp. 6845–6851.

Pascale Ghillani et al., "Monoclonal Antipeptide Antipeptide Antibodies As Tools To Dissect Closely Related Gene Products," The Journal of Immunology, vol. 141, No. 9, Nov. 1, 1988, pp. 3156–3163.

Dr. Sebastian Messerschmid, "Erzeugung von polyklonalen Antikörpern in Nicht–Säugern," BIOforum, Nov. 1996, pp. 500–502.

James W. Larrick et al., "Recombinant antibodies," Review, vol. 2, Oct. 1991, pp. 172–189.

Kazuaki Kitano et al., "Production of human monoclonal antibodies by heterohybridomas," Appl Microbiol Biotechnol, vol. 24, 1986, pp. 282–286.

Keith M. Thompson et al., "The efficient production of stable, human monoclonal antibody–secreting hybridomas from EBV–transformed lymphocytes using the mouse myeloma X63–Ag8.653 as a fusion partner," Journal of Immunological Methods, vol. 94, 1996, pp. 7–12.

Rainer Fischer et al., "Molecular Farming of Recombinant Antibodies in Plants," Biol. Chem., vol. 380, Jul./Aug. 1999, pp. 825–839.

Andrew Hiatt et al., "Assembly of Antibodies and Mutagenized Variants in Transgenic Plants and Plant Cell Cultures," Genetic Engineering, vol. 14, 1992, pp. 49–64.

R.C. Boguslaski et al., "Homogeneous Immunoassays," Applied Biochemistry and Biotechnology, vol. 7, 1982, pp. 401–414.

Edwin F. Ullman et al., "Luminescent oxygen channeling immunoassay: Measurement of particle binding kinetics by chemiluminescence," Proc. Natl. Acad. Sci, USA, vol. 91, Jun. 1994, pp. 5426–5430.

Edwin F. Ullman et al., "Luminescent oxygen channeling assay (LOCI™): sensitive, broadly applicable homogeneous immunoassay method," Clinical Chemistry, vol. 42, No. 9, 1996, pp. 1518–1526.

M. Philip Bailey et al., "On the use of fluorescent labels in immunoassay," Journal of Pharmaceutical & Biomedical Analysis, vol. 5, No. 7, 1987, pp. 649–658.

(List continued on next page.)

Primary Examiner—Christina Chan
Assistant Examiner—Phuong N. Huynh
(74) Attorney, Agent, or Firm—Finnegan, Henderson, Farabow, Garrett and Dunner, L.L.P.

(57) ABSTRACT

The invention relates to anti-procalcitonin antibodies, their preparation and use, in particular in therapy and diagnostics. The antibodies comprise binding to procalcitonin but not to free calcitonin, free katacalcin and free N-procalcitonin.

11 Claims, 1 Drawing Sheet

OTHER PUBLICATIONS

Figure 1:
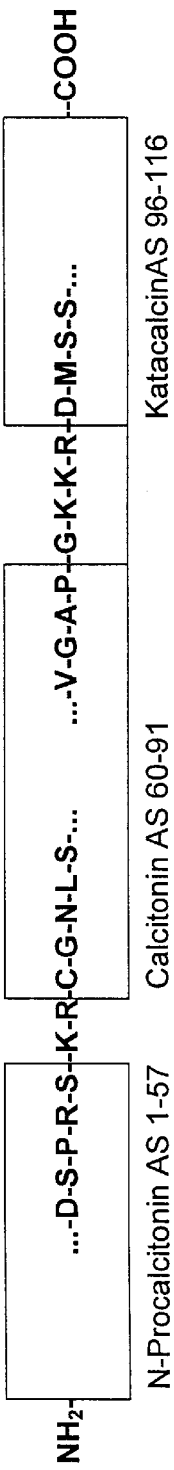

Sidney Udenfriend et al., "Scintillation proximity radioimmunology utilizing $^{125}$I–labeled ligands," *Proc. Natl. Acad. Sci, USA,* vol. 82, Dec. 1985, pp. 8672–8676.

Gérard Mathis, "Rare Earth Cryptates and Homogeneous Fluoroimmunoassays with Human Sera," *Clin. Chem,* vol. 39, No. 9, pp. 1953–1959.

* cited by examiner

ANTI-PROCALCITONIN ANTIBODIES AND THE PREPARATION AND USE THEREOF

The invention relates to anti-procalcitonin antibodies, their preparation and use.

BACKGROUND OF THE INVENTION

Procalcitonin ("pCT") is a protein consisting of 116 amino acids and having a molecular weight of about 13,000 Daltons. It is the prohormone of calcitonin which under normal metabolic conditions is produced and secreted by the C cells of the thyroid. pCT and calcitonin synthesis is initiated by translation of preprocalcitonin ("pre-pCT"), a precursor peptide comprising 141 amino acids. The amino acid sequence of human pre-pCT was described by Moullec et al. in FEBS Letters, 167:93–97 in 1984. pCT is formed after elimination of the signal peptide (first 25 amino acids of pre-pCT). In healthy people the hormone calcitonin (amino acids 60–91 of the pCT amino acid sequence), and N-procalcitonin (amino acids 1–57 of the pCT amino acid sequence) and katacalcin (amino acids 96–116 of the pCT amino acid sequence) are produced intracellularly from pCT by specific proteolysis (see also Conlan et al. (1988) Biochem. J., 256:245–250). pCT and fragments thereof were detected in increased concentrations in the serum or plasma of patients, in particular in cases of certain neoplastic diseases (Ghillani et al. (1989) Cancer Research, 49:6845–6851) and sepsis (EP-B1-0 656 121) and SIRS (systemic inflammatory response syndrome) (Snider et al. (1997) J. Investig. Med., 45:552–560).

During the typical sepsis bacteria are released continuously or in phases from a focus into the bloodstream. Endotoxin or other pyrogenic and toxic substances interacting with body mechanisms cause the clinical manifestations. The acute onset triggers chills and in severe cases a shock reaction. Special forms of septic shock are Waterhouse-Friderichsen syndrome and toxic shock syndrome (TSS). TSS is known as an acute clinical picture in staphylococcal infections which is caused by a specific staphylococcal toxin. A severe sepsis quite frequently develops in patients with serious primary disorders such as, for example, neoplastic diseases, serious burns and traumas.

The importance for sepsis diagnosis of detecting pathogens in the blood ("positive blood culture, bacteremia") has been pushed into the background, because in general the blood culture is positive only in 20 to 40% of sepsis cases. The term sepsis has therefore undergone a change. The modern term "sepsis" describes a clinical syndrome which in general comprises fever, leukocytosis, alterations of consciousness, a hyperdynamic circulation ("warm shock") and a hypermetabolic state, a positive blood culture no longer being required as a prerequisite for sepsis diagnosis.

WO 98/33524 suggests employing antibodies binding to pCT for the therapy of sepsis and SIRS.

Over many years polyclonal antibodies were obtained from immunization by calcitonin and used for detecting so-called immunoreactive calcitonin which, aside from calcitonin, also comprises procalcitonin and further procalcitonin fragments. Immunization by synthetic peptides having amino acid sequences corresponding to the sequence of procalcitonin segments succeeded in producing various monoclonal antibodies binding to various calcitonin and katacalcin epitopes (Ghillani et al. (1988) J. Immunol., 141:3156–3163).

On the basis of these antibodies sandwich immunoassays for detecting pCT and calcitonin in serum samples were also developed. A combination of an anti-katacalcin antibody and an anti-calcitonin antibody was suggested for detecting calcitonin precursor molecules (EP-B1-0 656 121). However, the disadvantage of such a method is that pCT detection requires at least two antibodies having to bind to pCT segments which are as far apart as possible.

It is therefore an object for the skilled worker to provide other specific binding partners which allow pCT detection even by just one specific binding partner.

This object is achieved by providing the antibodies according to the invention which bind to procalcitonin but not to free calcitonin which consists of amino acids 1–57 of procalcitonin, free katacalcin and free N-procalcitonin. In accordance with the invention, antibodies binding to a peptide having the amino acid sequence Asp-Ser-Pro-Arg-Ser-Lys-Arg-Cys-Gly-Asn-Leu-Ser (SEQ ID NO: 2) and antibodies binding to a peptide having the amino acid sequence Val-Gly-Ala-Pro-Gly-Lys-Lys-Arg-Asp-Met-Ser-Ser (SEQ ID NO: 4) are preferred.

In contrast to antibodies known so far which bind pCT but also at the same time bind free calcitonin or free katacalcin or free N-procalcitonin, the antibodies according to the invention may also be employed on their own for specific pCT detection in competitive assays or immunohistochemical methods. In addition, the antibodies according to the invention are particularly suitable for purifying pCT from a sample also containing pCT fragments by affinity chromatography.

Although Ghillani et al. in their immunization experiments employed peptides comprising the amino acid sequence Pro-Gly-Lys-Lys-Arg-Asp (SEQ ID NO: 3) or the amino acid sequence Val-Gly-Ala-Pro-Gly-Lys-Lys-Arg-Asp-Met-Ser-Ser (SEQ ID NO: 4), they only succeeded in providing antibodies recognizing either "mature" calcitonin or pCT together with calcitonin or pCT together with katacalcin, despite intensive efforts to identify the pCT epitopes.

BRIEF SUMMARY OF THE INVENTION

Surprisingly, antibodies have now been successfully created which bind to procalcitonin but not to free calcitonin, free katacalcin and free N-procalcitonin.

Specific embodiments of the invention are described in more detail below:

The invention relates preferably to such antibodies which bind procalcitonin but not free calcitonin, free katacalcin and free N-procalcitonin.

DETAILED DESCRIPTION OF THE INVENTION

The term "antibody" in accordance with this invention means an immunoglobulin, for example an immunoglobulin of the class or subclass IgA, IgD, IgE, $IgG_1$, $IgG_{2a}$, $IgG_{2b}$, $IgG_3$, $IgG_4$, IgM. An antibody comprises at least one binding site (often called paratope) for an epitope (often also called antigenic determinant) on an antigen or hapten. Such an epitope is characterized, for example, by its three-dimensional structure and/or the presence of polar and/or apolar groups. The antibody binding site is complementary to the epitope. The antigen-antibody reaction or hapten-antibody reaction works according to the so-called "lock-and-key principle" and is, in general, specific to a high degree, i.e. the antibodies are capable of distinguishing small differences in primary structure, charge, three-dimensional configuration and steric arrangement of the antigen or hapten. In particular the so-called complementarity determining regions of the antibody contribute to the binding of the antibody to the antigen or hapten.

The term "antigens" comprises monovalent and polyvalent antigens. A polyvalent antigen is a molecule or a molecule complex to which more than one immunoglobulin can bind simultaneously, whereas only a single antibody can bind to a monovalent antigen at any one time. A hapten usually denotes a molecule which on its own is not immunogenic but is usually bound to a carrier for immunization purposes.

The term antibodies in accordance with this invention means not only complete antibodies but expressly also antibody fragments such as, for example, Fab, Fv, F(ab')$_2$, Fab'; and also chimeric, humanized, bi- or oligo-specific or single-chain antibodies; furthermore also aggregates, polymers and conjugates of immunoglobulins and/or fragments thereof as long as the binding properties to the antigen or hapten are maintained. Antibody fragments can be prepared for example by enzymatic cleavage of antibodies using enzymes such as pepsin or papain. Antibody aggregates, polymers and conjugates can be generated by a multiplicity of methods, for example by heat treatment, reaction with substances such as glutaraldehyde, reaction with immunoglobulin-binding molecules, biotinylation of antibodies and subsequent reaction with streptavidin or avidin, etc.

An antibody in accordance with this invention can be a monoclonal or a polyclonal antibody. The antibody may have been prepared according to the usual processes, for example by immunization of humans or an animal such as, for example, mouse, rat, guinea pig, rabbit, horse, sheep, goat, chicken (see also Messerschmid (1996) BIOforum, 11:500–502) and subsequent preparation of the antiserum; or by establishing hybridoma cells and subsequent purification of the secreted antibodies; or by cloning and expression of nucleotide sequences or modified versions thereof coding for the amino acid sequences which are responsible for binding of the natural antibody to the antigen and/or hapten.

"Free" calcitonin, katacalcin and N-procalcitonin mean the pCT cleavage products calcitonin, katacalcin and N-procalcitonin which have been described further above and which may be formed in vivo by proteolysis of pCT.

Very preferred antibodies in accordance with this invention are antibodies binding to a peptide having the amino acid sequence Asp-Ser-Pro-Arg-Ser-Lys-Arg-Cys-Gly-Asn-Leu-Ser (SEQ ID NO: 2)or to a peptide having the amino acid sequence Val-Gly-Ala-Pro-Gly-Lys-Lys-Arg-Asp-Met-Ser-Ser (SEQ ID NO: 2). Further preferred antibodies in accordance with this invention are antibodies binding to a peptide having the amino acid sequence Arg-Ser-Lys-Arg-Cys-Gly (SEQ ID NO: 1) or to a peptide having the amino acid sequence Pro-Gly-Lys-Lys-Arg-Asp (SEQ ID NO: 3).

Particularly preferred antibodies in accordance with this invention are also pCT-binding antibodies produced by the hybridoma cell line 98-31/04. This hybridoma cell line was deposited with the DSMZ—Deutsche Sammlung von Mikroorganismen und Zellkulturen GmbH, Mascheroder Wet 1b Braunschweig, Germany under accession number DSM ACC2437 on Dec. 16, 1999.

This invention further relates to specific binding partners which bind to an epitope recognized by an antibody according to the invention.

A "specific binding partner" means a member of a specific binding pair. The members of a specific binding pair are two molecules each having at least one structure complementary to a structure of the other molecule, the two molecules being able to bind to each other via binding of the complementary structures. The term molecule also comprises molecule complexes such as, for example, enzymes comprising apoenzyme and coenzyme, proteins comprising a plurality of subunits, lipoproteins comprising protein and lipids, etc. Specific binding partners may be naturally occurring substances but also substances prepared by means of, for example, chemical synthesis, microbiological techniques and/or genetic engineering processes. Examples which may be mentioned to illustrate but not restrict the term specific binding partner are: thyroxine-binding globulin, steroid-binding proteins, antibodies, antigens, haptens, enzymes, lectins, nucleic acids, repressors, oligonucleotides and polynucleotides, protein A, protein G, avidin, streptavidin, biotin, complement component C1q, nucleic acid-binding proteins, etc. Specific binding pairs are for example: antibody/antigen, antibody/hapten, operator/repressor, nuclease/nucleotide, biotin/avidin, lectin/polysaccharide, steroid/steroid-binding protein, active ingredient/active ingredient receptor, hormone/hormone receptor, enzyme/substrate, IgG/protein A, complementary oligonucleotides or polynucleotides, etc.

It is now possible for the skilled worker, by providing the antibodies according to the invention, to identify, for example by competition experiments (see also Peters et al. (1985) Monoklonale Antikorper, Springer Verlag, section 12.2 "Epitop-Analyse"), other specific binding partners expressly including antibodies which bind to the epitope of an antibody according to the invention. Thus it is possible by techniques known to the skilled worker to select specific binding partners using phage display libraries, synthetic peptide databases or recombinatorial antibody libraries (Larrick & Fry (1991) Human Antibodies and Hybridomas, 2:172–189).

This invention also relates to an antibody according to the invention or a specific binding partner according to the invention being associated with a solid phase and/or a reporter system component.

The term "solid phase" in accordance with this invention comprises an object which consists of porous and/or nonporous, generally water-insoluble material and which may have very diverse shapes such as, for example, vessel, test tube, microtiter plate, bead, microparticle, stick, strip, filter paper or chromatography paper, etc. In general the surface of the solid phase is hydrophilic or may be made hydrophilic. The solid phase may comprise very diverse materials such as, for example, inorganic and/or organic materials, synthetic materials, naturally occurring materials and/or modified naturally occurring materials. Examples of solid-phase materials are polymers such as, for example, cellulose, nitrocellulose, cellulose acetate, polyvinyl chloride, polyacrylamide, crosslinked dextran molecules, agarose, polystyrene, polyethylene, polypropylene, polymethacrylate or nylon; ceramic; glass; metals, in particular noble metals such as gold and silver; magnetite; mixtures or combinations thereof; etc. The term solid phase also comprises cells, liposomes or phospholipid vesicles.

The solid phase may have a coating of one or more layers of, for example, proteins, carbohydrates, lipophilic substances, biopolymers, organic polymers or mixtures thereof in order to suppress or prevent, for example, non-specific binding of sample constituents to the solid phase or to achieve, for example, improvements in suspension stability of particulate solid phases, shelf life, shaping stability or resistance to UV light, microbes or other destructive agents.

A "reporter system" may be one or more components, at least one component being a detectable label. A label means any molecule producing a signal by itself or capable of inducing production of a signal such as, for example, a fluorescent substance, radioactive substance, enzyme or chemiluminescent substance. The signal may be detected or measured, for example, by the enzyme activity, luminescence, light absorption, light scattering, electromagnetic or radioactive emission or a chemical reaction.

A label may be able to produce a detectable signal by itself so that no further components are necessary. Many organic molecules absorb ultraviolet and visible light, it being possible for these molecules to reach an excited energy level due to the energy transferred by light absorption and to emit the absorbed energy as light of a wavelength different from that of the incident light. Yet other labels may produce directly a detectable signal such as, for example, radioactive isotopes or dyes.

Yet other labels need additional components for signal production, that is to say the signal-producing system in that case includes all components needed for generating the signal such as, for example, substrates, coenzymes, quenchers, accelerators, additional enzymes, substances reacting with enzyme products, catalysts, activators, cofactors, inhibitors, ions, etc.

Suitable labels (see also EP-A2-0 515 194; U.S. Pat. Nos. 5,340,716; 5,545,834; Bailey et al. (1987) J. Pharmaceutical & Biomedical Analysis 5:649–658) are, for example, enzymes including horseradish peroxidase, alkaline phosphatase, glucose-6-phosphate dehydrogenase, alcohol dehydrogenase, glucose oxidase, β-galactosidase, luciferase, urease and acetylcholinesterase; dyes; fluorescent substances including fluorescein isothiocyanate, rhodamine, phycoerythrin, phycocyanin, ethidium bromide, 5-dimethylaminonaphthalene-1-sulfonyl chloride and fluorescent rare earth chelates; chemiluminescent substances including luminol, isoluminol, acridine compounds, olefin, enol ether, enamine, aryl vinyl ether, dioxene, arylimidazole, lucigenin, luciferin and aequorin; sensitizers including eosin, 9,10-dibromoanthracene, methylene blue, porphyrin, phthalocyanin, chlorophyll, Rose Bengal; coenzymes; enzyme substrates; radioactive isotopes including $^{125}$I, $^{131}$I, $^{14}$C, $^{3}$H, $^{32}$P, $^{35}$S, $^{14}$C, $^{51}$Cr, $^{59}$Fe, $^{57}$Co, and $^{75}$Se; particles including magnetic particles or particles, preferably latex particles, which may be labeled themselves by, for example, dyes, sensitizers, fluorescent substances, chemiluminescent substances, isotopes or other detectable labels; sol particles including gold and silver sols; liposomes or cells which may be labeled themselves by detectable labels; etc.

A reporter system may also comprise components which can interact with each other in a detectable manner at close range, for example as energy donors and energy acceptors such as, for example, photosensitizers and chemiluminescent substances (EP-A2-0 515 194), photosensitizers and fluorophores (WO 95/06877), radioactive iodine-125 and fluorophores (Udenfriend et al. (1985) Proc. Natl. Acad. Sci. 82:8672–8676), fluorophores and fluorophores (Mathis (1993) Clin. Chem. 39:1953–1959) or fluorophores and fluorescence quenchers (U.S. Pat. No. 3,996,345).

An interaction between the components includes direct energy transfer between the components, for example by light or electron radiation and via short-lived reactive chemical molecules. It further comprises also processes in which the activity of one component is inhibited or enhanced by one or more others, for example inhibition of or increase in enzyme activity or inhibition of, increase or change in electromagnetic radiation emitted from the affected component (e.g. wavelength shift, polarization). The interaction between the components also comprises enzyme cascades. In this case the components are enzymes, at least one of which supplies the substrate for a second one, resulting in maximum or minimum reaction velocity of the coupled substrate conversion.

An effective interaction between the components generally takes place when these are in spatial proximity, that is, for example, within a distance of a few µm, in particular within a distance of below 600 nm, preferably below 400 nm, very particularly preferably below 200 nm.

Microparticles are commonly used as solid phase and/or label. The term "microparticle" in accordance with this invention means particles having an approximate diameter of at least 20 nm and no more than 20 µm, usually between 40 nm and 10 µm, preferably between 0.1 and 10 µm, particularly preferably between 0.1 and 5 µm, very particularly preferably between 0.15 and 2 µm. The microparticles may be shaped regularly or irregularly. They may comprise spheres, spheroids, spheres having more or less large cavities or pores. The microparticles may comprise organic material, inorganic material or a mixture or combination of both. They may comprise porous or nonporous material, swellable or non-swellable material. In principle the microparticles may have any density; however, particles having a density close to the density of water such as from about 0.7 to about 1.5 g/ml are preferred. The preferred microparticles are suspendable in aqueous solutions and stable in suspension for as long as possible. They may be transparent, partly transparent or opaque. The microparticles may comprise a plurality of layers such as, for example, the so-called core-and-shell particles having a core and one or more surrounding layers. The term microparticle comprises, for example, dye crystals, metal sols, silica particles, glass particles, magnetic particles, polymer particles, oil drops, lipid particles, dextran, and protein aggregates. Preferred microparticles are particles suspendable in aqueous solutions and comprising water-insoluble polymer material, in particular substituted polyethylenes. Very particularly preferred are latex particles made of, for example, polystyrene, acrylic acid polymers, methacrylic acid polymers, acrylonitrile polymers, acrylonitrile/butadiene/styrene, polyvinyl acetate/acrylate, polyvinylpyridine, vinyl chloride/acrylate. Of particular interest are latex particles having on their surface reactive groups such as, for example, carboxyl, amino or aldehyde groups which facilitate covalent binding, for example of specific binding partners, to the latex particles. The preparation of latex particles is described in, for example, EP 0 080 614, EP 0 227 054 and EP 0 246 446.

The term "associated" has a broad meaning and comprises, for example, covalent and noncovalent binding, direct and indirect binding, adsorption to a surface and enclosure in a depression or cavity, etc. In the case of covalent binding the antibodies or binding partners are bound to the solid phase or label via a chemical bond. Examples of noncovalent binding are surface adsorption, enclosure in cavities or binding of two specific binding partners. Apart from directly binding to the solid phase or the label, the antibodies or binding partners may also be bound indirectly to the solid phase or the label through specific interaction with other specific binding partners (see also EP-A2-0 411 945). This is to be illustrated in more detail with examples: the biotinylated antibody may be bound to the label via label-bound avidin; or a conjugate of fluorescein and antibody may be bound to the solid phase via solid-phase-bound anti-fluorescein antibodies; or the antibody may be bound to the solid phase or the label via immunoglobulin-binding proteins.

This invention further relates to antibodies or specific binding partners according to the invention which are used as an in vitro or in vivo diagnostic agent or as an ingredient of an in vitro or in vivo diagnostic agent.

In the case of an in vivo diagnostic agent the antibody according to the invention or the specific binding partner according to the invention, for example labeled by a radioactive isotope, is administered to an organism such as, for example, a human or an animal. It accumulates preferably in those organs or tissues containing or producing pCT in increased amounts. By detecting locations having increased radiation intensity it is possible, for example, to localize pCT-producing tumor foci and to display them three-dimensionally using image-generating processes.

In the case of an in vitro diagnostic agent the analyte to be detected, for example procalcitonin, is detected in a sample outside a living human or animal organism or the concentration or amount thereof is determined.

A "sample" in accordance with the invention means the material presumably containing the substance to be detected (for examples of the term "analyte" see EP-A2-0 515 194, pages 8 to 15). The term sample comprises, for example, biological fluids or tissue, in particular of humans and animals such as blood, plasma, serum, sputum, exudate, bronchoalveolar lavage, lymph fluid, synovial fluid, seminal fluid, vaginal mucus, feces, urine, CSF, hairs, skin, tissue samples or tissue sections. Further comprised are cell culture samples, plant fluids or tissue, forensic samples, water and wastewater samples, foods, medicaments. The samples need to be pretreated where appropriate to make the analyte available for the detection method or to remove interfering sample constituents. Such a pretreatment of samples may include removal and/or lysis of cells, precipitation, hydrolysis or denaturation of sample constituents such as, for example, proteins, centrifugation of samples, treatment of the sample using organic solvents such as, for example, alcohols, in particular methanol; treatment of the sample using detergents. Often the sample is transferred into another, usually aqueous, medium which, if possible, ought not to interfere with the detection method.

The antibodies according to the invention and/or the specific binding partners according to the invention may be used in a method for the quantitative or qualitative detection of an analyte, preferably procalcitonin, in a sample.

In a quantitative test the amount or the concentration of the analyte in the sample is measured. The term "quantitative test" also comprises semiquantitative methods which may measure only the approximate amount or concentration of the analyte in the sample or serve only to indicate relative quantities or concentrations. A qualitative test means detecting the presence of the analyte in the sample in fact or indicating that the analyte concentration in the sample is below or above a particular threshold or several particular thresholds.

Using the antibodies according to the invention and/or the specific binding partners according to the invention it is possible to detect pCT, for example, immunohistochemically in smears, tissue sections or tissue samples. Thus, for example, cryosections or paraffin sections are prepared from the tissue to be examined. The sections are incubated with the antibodies according to the invention under suitable reaction conditions. After washing off the unbound antibodies according to the invention, the areas to which the antibodies according to the invention have bound are detected. If the antibodies are provided with, for example fluorescent labels, no further intermediate steps need take place. Alternatively, the bound antibodies according to the invention may be detected using appropriate specific binding partners which are associated with a label and are able to bind to the bound antibodies according to the invention.

The detection of pCT with the antibodies according to the invention and/or the specific binding partners according to the invention may be carried out by methods such as, for example: Western blot, dot blot, immunoelectrophoresis, immunofixation electrophoresis, electroimmunodiffusion, immunoprecipitation, radial immunodiffusion, immunofixation, immunochromatography, latex agglutination, turbidimetric or nephelometric test, homogeneous or heterogeneous binding assay, one- or two-step assay, sandwich assay, indirect assay, competitive assay, point-of-care tests, etc. These and other detection methods are described, for example, in "Labor und Diagnose", ed. L. Thomas, TH-Books Verlagsgesellschaft mbH, Frankfurt, 1998, chapter 60, or in "Laboratory Techniques in Biochemistry and Molecular Biology—An Introduction to Radioimmunoassay and Related Techniques", ed. T. Chard, Elsevier, Amsterdam, 1987.

In binding assays the analyte, if present in the sample, is bound to one or more analyte-specific binding partners, and analyte/analyte-specific binding partner(s) complexes are formed.

In homogeneous binding assays free and complex-bound analytes are not separated. Examples of homogeneous immunoassays (see also Boguslaski & Li (1982) Applied Biochemistry and Biotechnology, 7:401–414) are many turbidimetric or nephelometric methods, it being possible for the specific binding partners used for the detection to be associated with latex particles; EMIT® assays; CEDIA® assays; fluorescence polarization immunoassays; luminescent oxygen channeling immunoassays (EP-A2-0 515 194; Ullman et al. (1994) Proc. Natl. Acad. Sci., 91:5426–5430; Ullman et al. (1996) Clinical Chemistry, 42:1518–1526); etc.

Heterogeneous binding assays comprise one or more separation steps and/or wash steps. The separation may be carried out by, for example, immunoprecipitation, precipitation using substances such as polyethylene glycol or ammonium sulfate, filtration, magnetic separation, binding to a solid phase such as, for example, to a test tube, a bead, a well of a microtiter plate or to filter paper or chromatography paper. In heterogeneous binding assays frequently one specific binding partner is associated with a reporter system component and one specific binding partner is associated with a solid phase (regarding indirect binding see also EP-A2-0 411 945). Here the specific binding partners may be different or the same, for example an analyte-specific monoclonal antibody may be employed both as capture agent (for example as a solid-phase antibody) and as labeled antibody if the analyte contains more than one epitope.

In heterogeneous sandwich assays the analyte is usually bound by a specific binding partner associated with a solid phase and a specific binding partner associated with a reporter system component. In the case of a sandwich immunoassay the specific binding partners may be analyte-specific antibodies or, if the analyte itself is an antibody, the antigen and/or a "modified antigen", for example a labeled antigen, antigen fragment, antigen analog. Examples of such sandwich complexes are: solid-phase antibody<>analyte<>antibody label or solid-phase antigen<>analyte (=antibody)<>antigen label.

A further embodiment of a heterogeneous immunoassay is the indirect immunoassay: in this case the analyte is an antibody. One of the specific binding partners is the antigen thereof and/or a modified antigen and the other specific binding partner is an antibody binding to the analyte and/or an immunoglobulin-binding protein. Examples of such complexes which may be formed in an indirect immunoassay are: solid phase anti-immunoglobulin antibody <>analyte (=anti-pCT antibody)<>labeled pCT or, alternatively, solid phase pCT<>analyte (=anti-pCT antibody)<>labeled protein A.

In a heterogeneous competitive immunoassay the sample analyte competes with a "modified analyte", for example a labeled analyte, analyte fragment, analyte analog, etc. for a limited number of analyte-specific binding sites. Examples illustrating the principle are: (i) sample analyte competes with an analyte associated with a reporter system component for binding to a solid-phase associated analyte-specific antibody or (ii) sample analyte competes with a solid-phase associated analyte for binding to an analyte-specific antibody associated with a reporter system component.

Sandwich assays, competitive assays and indirect assays may also be carried out as homogeneous assay methods (see also EP-A2-0 515 194).

The term "point-of-care tests" or "POC tests" has a broad meaning. It includes tests which do not need a separate analyzing or measuring device for carrying out or evaluating the test. In many cases POC tests are based on immuno-chromatography methods, immune complex separations by filtration and/or immunofixation techniques. POC tests are intended in particular for on-the-spot measurements, for example at the hospital bed or at home, for the emergency doctor and/or the general practitioner and not so much for the large-scale laboratory. POC tests may also be carried out in particular by persons without in-depth training in medical technology and experience in the field of laboratory medicine. The term "POC tests" in accordance with this invention also means so-called home tests or OTC (over the counter) tests which may be carried out by medical lay-persons such as, for example, the various pregnancy tests sold for home use. Further POC tests relate to, for example, the detection of heart attack markers, drugs, medicaments, infection markers and inflammation markers. In many POC tests specific binding partners are associated to filter or chromatography strips or disks during the course of the test. A positive or negative test reaction may be linked, for example, to the appearance or nonappearance of a colored band in a particular test field and/or the appearance or nonappearance of a particular symbol, for example "+", "−" and/or the intensity of the respective measured signal.

A POC test for pCT, for example, may be constructed in the following way: the sample and labeled antibodies which are capable of binding to pCT are applied to a test strip. Suitable labels are, for example, colored latex particles, colloidal gold, enzymes, etc. If pCT is present in the sample, pCT/antibody complexes will be formed. These complexes move by means of capillary force toward a section where antibodies capable of binding to different pCT epitopes are fixed, for example as a band, or will be fixed during the course of the test (for example via a biotin/avidin bridge). The labeled PCT/antibody complexes are bound in this section and form a sandwich complex with the fixed antibodies. The intensity of the label signal is proportional to the pCT sample concentration in this case. In a competitive POC test method pCT and/or pCT fragments may be fixed, for example, in a section of the test strip or will be fixed in the course of the test. This fixed pCT would compete with pCT from the sample for binding to labeled anti-pCT antibodies. Alternatively, fixed anti-pCT antibodies and labeled pCT may also be employed for constructing a competitive pCT test.

A particularly preferred embodiment of the process according to the invention is a nephelometric or turbidimetric test, in particular a test which employs antibodies according to the invention and/or specific binding partners according to the invention, preferably associated to latex particles.

The invention further relates to a test kit containing one or more of the antibodies according to the invention and/or one or more of the specific binding partners according to the invention. Such a kit usually contains all or only some test components in packaged form. The antibodies according to the invention and the specific binding partners according to the invention may be associated to, for example, one or more solid phases and/or one or more reporter system components. The test kit may contain, for example, standards; controls; and further reagents such as, for example, buffers, washing solutions, measured-signal-inducing solutions and/or enzyme substrate; cuvettes; pipettes and/or instructions. A particularly preferred test kit according to the invention contains antibodies according to the invention associated to latex particles.

The antibodies according to the invention and specific binding partners according to the invention may also be used for affinity chromatography. The term "affinity chromatography" means a method by which substances, in particular biopolymers, are purified and isolated and which is based on the fact that many substances can bind to their specific binding partners in a selective, noncovalent, reversible manner. The principle of the process involves the specific binding partner being bound in general covalently to an insoluble matrix (e.g. porous glasses, gels based on agarose, cellulose, dextran, polymer and silica gel) and brought into contact with a sample containing the substance. The sought-after substance is immobilized and retained by its specific interaction with the matrix-bound specific binding partner, while all other substances contained in the sample are removed by elution. The sought-after biopolymer is then detached from the matrix using a suitable eluent which cancels out the noncovalent bond between substance and specific binding partner (see also E. Buddecke (1989) Grundrisse der Biochemie, Walter de Gruyter, chapter 7 "Proteine").

This invention further comprises antibodies according to the invention and/or specific binding partners according to the invention in a pharmaceutically suitable sterile injection medium. A pharmaceutically suitable sterile injection medium means, for example, a sterile pyrogen-free solution, for example saline or another electrolyte solution, such as is used conventionally in the intravenous, intramuscular, intraperitoneal or subcutaneous administration of medicaments, vaccines or contrast media.

This invention additionally relates to the use of the antibodies according to the invention and/or the specific binding partners according to the invention as a diagnostic agent, as an ingredient of a diagnostic agent, as a medicament or as an ingredient of a medicament. The invention also includes the use of the antibodies according to the invention and/or the specific binding partners according to the invention for the treatment of SIRS (systemic inflammatory response syndrome), sepsis and/or tumors, in particular malignant pCT-producing tumors. SIRS is a systemic inflammatory response to tissue damage with symptoms of a remote organ dysfunction. The invention further includes a process for preparing a medicament, for example for the treatment of tumors, sepsis and/or SIRS, containing the antibodies according to the invention and/or the specific binding partners according to the invention.

The antibodies according to the invention and/or the specific binding partners according to the invention may be employed for treatment intracorporeally or else extracorporeally. The antibodies according to the invention and/or the specific binding partners according to the invention may have their activity enhanced by radioactive isotopes and/or linking to pharmacologically active substances. WO 98/33524 describes the therapeutic application of anti-pCT antibodies in more detail. Moreover, pCT could be removed from a patient's blood for example by a process analogous to dialysis, the blood or plasma being brought into contact extracorporeally with sterile and fixed antibodies according to the invention and/or specific binding partners according to the invention This invention further relates to a process for preparing an antibody according to the invention which comprises using for the immunization one or more peptides which comprise the amino acid sequence Arg-Ser-Lys-Arg-Cys-Gly (SEQ ID NO: 1), preferably the amino acid sequence Asp-Ser-Pro-Arg-Ser-Lys-Arg-Cys-Gly-Asn-Leu-Ser (SEQ ID NO: 2), and/or the amino acid sequence Pro-Gly-Lys-Lys-Arg-Asp (SEQ ID NO: 3), preferably the amino acid sequence Val-Gly-Ala-Pro-Gly-Lys-Lys-Arg-Asp-Met-Ser-Ser (SEQ ID NO: 4). In a preferred process according to the invention at least one of the peptides used for immunization is an oligopeptide, preferably a carrier-bound oligopeptide. A further preferred process for preparing an antibody according to the invention comprises the use for immunization of one or more peptides having the amino acid sequence Arg-Ser-Lys-Arg-Cys-Gly (SEQ ID NO: 1), the amino acid sequence Asp-Ser-Pro-Arg-Ser-Lys-Arg-Cys-Gly-Asn-Leu-Ser (SEQ ID NO: 2), the amino acid sequence Pro-Gly-Lys-Lys-Arg-Asp (SEQ ID NO: 3) and/or the amino acid sequence Val-Gly-Ala-Pro-Gly-Lys-Lys-Arg-Asp-Met-Ser-Ser (SEQ ID NO: 4), it being possible for these peptides also to be carrier-bound. The antibodies according to the invention may also be prepared by using naturally occurring and/or recombinant pCT as immunization antigen. Furthermore, peptides may also be used for immunization containing one or more of the following amino acid sequences repetitively, Arg-Ser-Lys-Arg-Cys-Gly (SEQ ID NO: 1), Asp-Ser-Pro-Arg-Ser-Lys-Arg-Cys-Gly-Asn-Leu-Ser (SEQ ID NO: 2), Pro-Gly-Lys-Lys-Arg-Asp (SEQ ID NO: 3) and/or Val-Gly-Ala-Pro-Gly-Lys-Lys-Arg-Asp-Met-Ser-Ser (SEQ ID NO: 4), for example Arg-Ser-Lys-Arg-Cys-Gly-Arg-Ser-Lys-Arg-Cys-Gly or Asp-Ser-Pro-Arg-Ser-Lys-Arg-Cys-Gly-Asn-Leu-Ser-Arg-Ser-Lys-Arg-Cys-Gly-Arg-Ser-Lys-Arg-Cys-Gly or Asp-Ser-Pro-Arg-Ser-Lys-Arg-Cys-Gly-Asn-Leu-Ser-Asp-Ser-Pro-Arg-Ser-Lys-Arg-Cys-Gly-Asn-Leu-Ser-Val-Gly-Ala-Pro-Gly-Lys-Lys-Arg-Asp-Met-Ser-Ser-Val-Gly-Ala-Pro-Gly-Lys-Lys-Arg-Asp-Met-Ser-Ser. amino acid sequences repetitively, Arg-Ser-Lys-Arg-Cys-Gly (SEQ ID NO: 1), Asp-Ser-Pro-Arg-Ser-Lys-Arg-Cys-Gly-Asn-Leu-Ser (SEQ ID NO: 2), Pro-Gly-Lys-Lys-Arg-Asp and or Val-Gly-Ala-Pro-Gly-Lys-Lys-Arg-Asp-Met-Ser-Ser, (SEQ ID NO: 4) for example Arg-Ser-Lys-Arg-Cys-Gly-Arg-Ser-Lys-Arg-Cys-Gly or Asp-Ser-Pro-Arg-Ser-Lys-Arg-Cys-Gly-Asn-Leu-Ser-Arg-Ser-Lys-Arg-Cys-Gly -Arg-Ser-Lys-Arg-Cys-Gly or Asp-Ser-Pro-Arg-Ser-Lys-Arg -Cys-Gly-Asn-Leu-Ser-Asp-Ser-Pro-Arg-Ser-Lys-Arg-Cys -Gly-Asn-Leu-Ser-Val-Gly-Ala-Pro-Gly-Lys-Lys-Arg-Asp -Met-Ser-Ser-Val-Gly-Ala-Pro-Gly-Lys-Lys-Arg-Asp-Met -Ser-Ser.

The term "peptides" in accordance with this invention comprises amides which decompose into amino acids on hydrolysis, for example amino acid polymers such as, for example, polypeptides, oligopeptides, proteins or protein fragments. Molecules with no more than ten linked amino acids are in general called oligopeptides, with more than that they are called polypeptides. Oligopeptide according to the definition of this invention also comprises amino acid chains of up to about 20 amino acids.

This invention also relates to the two oligopeptides having the amino acid sequence Asp-Ser-Pro-Arg-Ser-Lys-Arg-Cys-Gly-Asn-Leu-Ser (SEQ ID NO: 2) and the amino acid sequence Val-Gly-Ala-Pro-Gly-Lys-Lys-Arg-Asp-Met-Ser-Ser (SEQ ID NO: 4). These peptides may be used as immunization antigen for preparing the antibodies according to the invention.

The peptides used as immunization antigen may be used for the immunization in unbound and/or carrier-bound form. Typical carriers are, for example, proteins such as, for example, ovalbumin, albumin or hemocyanin, or polymers such as, for example, polyethylene glycol, polyacrylamide or poly-d-glutamine-d-lysine. The peptides can be bound to this carrier, for example, using carbodiimide or glutaraldehyde or else using a bifunctional reagent which can also act as a spacer (for examples and coupling methods see e.g. Wong S. (1993) Chemistry of Protein Conjugation and Cross-Linking, CRC Press Inc., Boca Raton).

The immunization antigen, for example, may be suspended in phosphate-buffered saline and treated with Freund's adjuvant. This emulsion may then be administered, for example, intradermally, intraperitoneally and/or subcutaneously to an animal, for example a rabbit, mouse, rat, guinea pig, horse, sheep, goat, chicken, etc. Booster injections may help to increase the immune response, it also being possible for the immunization antigen to be emulsified with incomplete Freund's adjuvant.

Polyclonal antibodies according to the invention may be obtained from the antiserum of the immunized animals. These antibodies can be further purified by means of affinity chromatography on a matrix to which, for example, pCT or the peptides employed as immunization antigen have been bound.

In order to create monoclonal antibodies according to the invention the immune cells of immunized animals such as, for example, a mouse, are fused according to generally well-known methods (see e.g. Harlow & Lane (1988) Antibodies: A Laboratory Manual, Cold Spring Harbor Laboratory, Cold Spring Harbor; Peters et al. (1985) Monoklonale Antikörper: Herstellung und Charakterisierung, Springer Verlag) with myeloma cells to create hybridoma cells producing monoclonal antibodies (MAb), and subsequently suitable clones are isolated. The desired MAb-producing clones are selected using specific screening methods. In these methods the binding specificity of the antibodies released into the cell culture supernatant, for example for the immunization antigen, for a possible carrier of the immunization antigen, for pCT, for free calcitonin, for free katacalcin and for free N-procalcitonin, is tested using, for example, enzyme immunoassays, radioimmuno-assays and/or Western blots. Hybridomas producing antibodies according to the invention are cloned. The hybridoma cell lines obtained in this way are then available for continuous MAb production. Larger quantities of antibodies may be obtained from, for example, cell culture supernatant, in particular from fermenters or roller cultures and from ascites.

It is advantageous, depending on the desired application, to employ only antibody fragments such as, for example, Fab, F(ab')$_2$ or Fab' fragments. These may be created, for example, by enzymatic cleavage methods known to the skilled worker (see also e.g. Harlow & Lane (1988) Antibodies: A Laboratory Manual, Cold Spring Harbor Laboratory, Cold Spring Harbor).

The antigen binding sites of an antibody are located in the so-called variable domains coded for by the V genes. Using well-known genetic engineering methods (see e.g. Sambrook et al. (1989) Molecular Cloning: A Laboratory Manual, Cold Spring Harbor Laboratory, Cold Spring Harbor, 2nd edition; McCafferty et al. (1990) Nature 348:552–554) it is also possible to determine the corresponding nucleic acid sequence of an antibody according to the invention and thereby also the corresponding amino acid sequence, if not already known from amino acid sequencing. For analyses of this kind, the hybridoma cells or the antibody-producing immune cells of immunized animals may be employed as starting material.

Knowing the nucleic acid sequence and/or amino acid sequence it is then possible using conventional genetic engineering and molecular biology methods (see also Johnson & Chiswell (1993) Current Opinion in Structural Biology, 3:564–571) to prepare humanized, chimeric, bi- or oligo-specific antibodies and peptides derived from the complementarity determining region (minimal recognition units), single-chain fragments and/or functional fusion products, for example recombinant antibody-enzyme constructs (see e.g. Larrick & Fry (1991) Human Antibodies and Hybridomas, 2:172–189; Kitano et al. (1986) Appl. Microbiol. Biotechnol., 24:282–286; Thompson et al. (1986) J. Immunol. Methods, 94:7–12) which bind to procalcitonin but not to free calcitonin, free katacalcin and free N-procalcitonin. Using such peptides included in the term "antibody" it is possible, for example, to achieve a decrease in immunogenicity and/or an enhanced efficiency when administered as a medicament or in vivo diagnostic agent and/or there will be advantages when employed as or as part of an in vitro diagnostic agent. The antibodies may also be prepared using, where appropriate, genetic engineering methods in plant cells such as, for example, yeast cells (Fischer et al. (1999) Biol. Chem., 380:825–839; Hiatt et al. (1992) Genetic Engineering, 14:49–64), animal and prokaryotic cells (see e.g. WO 95/25172) and isolated human cells.

Furthermore, this invention also relates to animal, plant or prokaryotic cells and isolated human cells producing an antibody according to the invention. A preferred embodiment of this invention comprises hybridoma cell lines producing the antibodies according to the invention, for example hybridoma cell line 98-31/04. This hybridoma cell line was deposited with the DSMZ Deutsche Sammlung von Mikroorganismen und Zellkulturen GmbH, Mascheroder Weg 1b Braunschweig, Germany, under accession number DSM ACC2437 on Dec. 16, 1999.

BRIEF DESCRIPTION OF THE SEVERAL VIEW OF THE DRAWING

FIG. 1 shows a diagrammatic representation of human pCT and its proteolytic cleavage products, showing the location of SEQ ID NO:2 (D-S-P-R-S-K-R-C-G-N-L-S) and SEQ ID NO:4 (V-G-A-P-G-K-K-R-D-M-S-S); AS=amino acids.

The examples described below serve as exemplary illustrations of individual aspects of this invention and are not to be understood as a restriction.

EXAMPLES

Example 1

Peptide Synthesis

Two peptides "P1" and "P2" corresponding to amino acids 53–64 and 88–99 of human procalcitonin (see also FIG. 1) and having the sequence:

P1:Asp-Ser-Pro-Arg-Ser-Lys-Arg-Cys-Gly-Asn-Leu-Ser (SEQ ID NO: 2)

P2:Val-Gly-Ala-Pro-Gly-Lys-Lys-Arg-Asp-Met-Ser-Ser (SEQ ID NO: 4)

were synthesized as follows:

P1 and P2 are synthesized in an Applied Biosystems peptide synthesizer, model 431A with 9-fluorenylmethyloxycarbonyl (fmoc) amino acid chemistry. The protective groups present were cleaved off by trifluoroacetic acid treatment.

Example 2

Coupling of Peptides to a Carrier

The peptides were coupled to bovine serum albumin (BSA, Centeon Pharma, Marburg, Germany) (see also Rusin et al. (1992) Biosens. Bioelectron., 7:367–373; Kitagawa et al. (1983) J. Biochem., 94:1165–1172).

In detail: 100 mg of BSA in 20 ml of 0.1 M lithium borate buffer pH 8.0 are mixed with 41.8 mg of N-gamma-maleimidobutyryloxysuccinimide (GMBS) (Calbiochem-Novabiochem GmbH, Bad Soden, Germany) and incubated at 20° C. for 30 minutes. Afterward, the reaction mixture is pH-adjusted with 0.1 M NaH$_2$(PO$_4$) pH 6.0 (BSA/GMBS solution). 7.5 mg of P1 or P2 are dissolved in 1.75 ml of 0.1 M lithium borate buffer pH 8.0, and 2.1 mg of S-acetylmercaptosuccinic anhydride (Fluka Chemie GmbH, Deisenhofen, Germany) dissolved in dioxane (22.2 mg/ml) are added and incubated at 20° C. for 30 minutes. Subsequently, 475 µl of 1 M hydroxylamine solution are added and incubated at 20° C. for a further 15 minutes. The resultant reaction mixture is mixed with 16 ml of BSA/GMBS solution and incubated at 20° C. for 2 hours. Afterward, the reaction is stopped by adding 0.1 M N-ethylmaleimide solution and pH-adjusted with phosphate-buffered saline pH 7.2.

Example 3

Preparation of Monoclonal Antibodies a) Immunization of Mice

BALB/c mice were each immunized intraperitoneally with 20 µg of P1/BSA conjugate or 20 µg of P2/BSA conjugate in complete Freund's adjuvant. A booster of 20 µg of P1/BSA conjugate or 20 µg of P2/BSA conjugate in incomplete Freund's adjuvant (ICN Biomedical GmbH, Eschwege, Germany) was given to each after 4 weeks and 20 µg of P1/BSA conjugate or 20 µg of P2/BSA conjugate without Freund's adjuvant was given to each after 8 weeks. On the last 3 days before fusion the mice were each boosted intravenously with 20µg of P1/BSA conjugate or 20µg P2/BSA conjugate.

b) Fusion

After sacrificing the mice by CO$_2$ inhalation the spleens were removed and single cell suspensions were prepared in serum-free Dulbecco's modified Eagle medium (DMEM, CC Pro GmbH, Neustadt/W, Germany). The cells were centrifuged (652×g) and washed twice in DMEM. Subsequently the cell number was determined by means of trypan blue staining. $2 \times 10^7$ myeloma cells (Sp2/0) were added to about $10^8$ spleen cells. After centrifugation (360×g) the supernatant was discarded, 1 ml of polyethylene glycol solution (PEG 4000, Merck Eurolab, Bruchsal, Germany; about 50% in DMEM) was added to the cell pellet, and the resuspended cells were incubated for 1 minute at 37° C. About 10 ml of DMEM were subsequently added dropwise and incubated at room temperature for 2 to 4 minutes. The fused cells were spun down (326×g) and the pellet was resuspended in DMEM+20% FBS (fetal bovine serum, BioWhittaker Europe, Verviers, Belgium) +HAT solution (CC Pro GmbH, Neustadt/W, Germany) and introduced into 24-well cell culture dishes (Costar). The approximate cell concentration per well was $5 \times 10^4$ to $5 \times 10^6$ cells.

2–3 weeks later the resulting cell colonies (hybrids) were removed and transferred into new culture dishes.

c) Determination of Antibody Specificity

The specificity of the antibodies released into the cell culture was tested in a first step using microtiter plates coated with immunization antigen (Nunc, type B), coating 0.2 µg/ml≈0.003 µg/well.

100 µl of cell culture supernatant (dilution 1:2) were pipetted into each well of the microtiter plate and incubated at +15 to +25° C. for 1 hour. After washing the plate twice using washing solution POD (OSEW; Dade Behring, Marburg, Germany) 100 µl of anti-mouse IgG/F(ab')$_2$-POD conjugate (Dade Behring, Marburg, Germany) were introduced into each well and incubated at +15 to +25° C. for 1 hour. After washing the plate twice again, 100 µl of Chromogen TMB solution (Dade Behring, Marburg, Germany) were introduced into each well and incubated at +15 to +25° C. for a further 30 minutes. After the incubation, 100 µl of stop solution POD (Dade Behring, Marburg, Germany) were introduced into each well and the microtiter plate was evaluated at 450 nm in a BEP II (Behring ELISA Processor II, Dade Behring, Marburg, Germany).

In a 2nd step the hybrids were tested as described above using microtiter plates (Nunc, type B) coated with the following peptides:

i. Recombinant human pCT (0.03 µg/well). The parallel application entitled "Human procalcitonin and the preparation and use thereof" filed at German Patent and Trademark Office on Dec. 22, 1999 (file reference 199 62 434.8) describes in detail the preparation of recombinant pCT. A plasmid suitable for the expression of pCT in E. coli was deposited with the DSMZ Deutsche Sammlung von Mikroorganismen und Zellkulturen GmbH under the number DSM 13203 on Dec. 16, 1999. This plasmid may be transformed into a suitable E. coli strain (e.g. JM109; Stratagene, LaJolla, USA) using standard methods (Current Protocols in Molecular Biology, Wiley, 1997). Clones may be obtained after plating the transformation mixture on LB agar plates containing 50 µg/ml ampicillin for selection. Procalcitonin may be expressed using the following procedure: JM109 cells freshly transformed with the expression plasmid are grown with shaking overnight in LB medium with 100 µg/ml ampicillin at 37° C. and then diluted 1:50 in 1 l of fresh LB medium (ampicillin 100 µg/ml) and further shaken at 37° C. and induced at an $OD_{600}$ of 0.4 with 2 mM IPTG for 3 h. By following these optimized conditions, about 13 mg of fusion protein were reproducibly obtained from a 1 l culture after purification under native conditions by metal affinity chromatography according to the manufacturer's instructions (Talon Metal Affinity Resin, Clontech, Palo Alto, USA) and subsequent gel filtration on Superdex 75 HiLoad (Amersham Pharmacia).

ii. Calcitonin human BSA conjugate (0.5 µg/well, Bachem, Prod. No.: H-2250)

iii. Katacalcin human (PDN-21) BSA conjugate (0.5 µg/well, Peninsula, Prod. No.: 6004)

iv. Calcitonin N-terminal flanking peptide BSA conjugate (0.5 µg/well, Bachem, Prod. No.: H-3076) =human N-procalcitonin The results are listed in Table 1.

TABLE 1

Determination of antibody specificity by evaluating the microtiter plates at 450 nm in a BEP II (Behring ELISA Processor II).

| Hybrid/clone | Peptide 1 | Peptide 2 | Recombinant human pro-calcitonin | Cal-citonin | Kata-calcin | N-pro-cal-citonin |
|---|---|---|---|---|---|---|
| 98-47/44 | 0.975 | negative | 0.100 | 0.561 | 2.5 | negative |
| 98-31/04 | negative | 1.715 | 0.290 | negative | negative | negative |
| 98-31/74 | negative | 2.374 | negative | 0.118 | 0.149 | negative | negative = extinction at 450 nm < 0.1 or no variation in signal on dilution of the hybrid studied d) Cloning Single hybrid cells producing the antibodies according to the invention (binding to human pCT but not to free calcitonin, free katacalcin and free N-procalcitonin) were cloned using a micromanipulator (Leitz, Wetzlar, Germany). The clone 98-31/04 obtained in this way was deposited with the DSMZ Deutsche Sammlung von Mikroorganismen und Zellkulturen GmbH, Mascheroder Weg 1b Braunschweig, Germany, under accession number DSM ACC2437 on Dec. 16, 1999.

e) Antibody Subclass Determination

The subclass of antibody 98-31/04 was determined as $IgG_1$, by means of the IsoStrip™-Mouse Monoclonal Antibody Isotyping Kit from Boehringer Mannheim, Germany.

f) Antibody Production

For the production of larger quantities of antibodies the corresponding cell clones are transferred to roller bottles (Corning Costar Deutschland, Bodenheim) and expanded to the desired final volume at +37° C. Afterward, the roller culture suspension is filtered through 0.22 µm to remove the cells. The now cell-free antibody solution is concentrated via ultrafilters (30,000 dalton cutoff) and subsequently purified.

g) Antibody Purification

The antibody solution obtained is pH-adjusted with 0.14 M phosphate buffer pH 8.6 and applied to a chromatography column packed with rProtein A Sepharose Fast Flow (Amersham Pharmacia) (1 ml of rProtein A Sepharose Fast Flow is employed per 10 mg of antibody to be purified). All unbound components are removed by washing the column with 0.14 M phosphate buffer pH 8.6. The bound antibody is eluted from the column by 0.1 M citric acid pH 3.0 and dialyzed against 0.05 M sodium acetate +0.5 M NaCl+0.05 M tris+0.01% sodium azide pH 7.0.

Example 4

Detection of pCT in a Sample a) MAb binding to Latex Particles

One monoclonal antibody according to the invention and one monoclonal anti-katacalcin antibody were bound to each latex particle prepared according to EP-0246 446 and having a diameter of from 250 to 310 nm:

The latex polymer used was diluted to a solids content of 4% by weight using distilled water. The antibodies to be bound were diluted to a protein content of 5 mg/ml using 0.05 M sodium acetate +0.5 M NaCl +0.05 M tris +0.01% sodium azide pH 7.0. 1 ml of the above-mentioned polymer was mixed with 200 µl of antibody solution. Then 0.050 ml of a 20% Tween 20 solution (Merck Eurolab, Darmstadt, Germany) was added and the mixture was mixed again. 0.025 ml of 1 N HCl was added thereto, resulting in a pH of about 3. After incubation at room temperature for 30 minutes, 0.25 ml of 1 M phosphate buffer pH 6.5 and 0.25 ml of sodium cyanoborohydride solution (25 mg/ml) were added and mixed well. This was followed by incubation at room temperature for one hour.

This loading mixture was then centrifuged at about 50,000×g for 30 minutes. The supernatant was discarded. The residue was resuspended in 4 ml of imidazole buffer pH 8.1 (5 g/l imidazole, 40 g/l sucrose, 1 g/l human albumin). This was followed by sonication (Branson Sonifier B15) for 30 seconds. The reagent redispersed in this way was diluted in a volume ratio of 1:7.5 using the imidazole buffer mentioned before and sonicated again for 30 seconds.

b) Detection of pCT

The reagents prepared according to Example 4a) by binding of the antibody according to the invention and the anti-katacalcin antibody to latex particles were mixed in a volume ratio of 1+1 and employed for measuring pCT in the sera of patients in a Behring Nephelometer Analyzer (BNA, Dade Behring, Marburg, Germany). The mixed reagent is agglutinated on mixing with pCT-containing samples. The intensity of the scattered light in the BNA is dependent on the sample pCT concentration. For the measurement, 100 µl of sample (1 normal serum, 3 pCT-containing samples from patients (BRAHMS LUMItest® PCT, >100 ng/ml pCT)) were mixed with 100 µl of N-Diluens (Dade Behring, Marburg, Germany) and 40 µl of the mixed reagent in a reaction cuvette and the change in the measured signal (in bit) was measured in the BNA after 12 minutes. The results are summarized in Table 2.

TABLE 2

| Sample | Measured signal BNA in bit |
| --- | --- |
| Normal serum | −58 |
| pCT-containing serum 1 | 212 |
| pCT-containing serum 2 | 197 |
| pCT-containing serum 3 | 592 |

We claim:

1. An antibody which binds to procalcitonin, but does not bind to free calcitonin, free katacalcin, or free N-procalcitonin.

2. The antibody according to claim 1 which binds to a peptide comprising the amino acid sequence SEQ ID NO: 4.

3. The antibody according to claim 1 which is produced by the hybridoma cell line 98-31/04 (DSM ACC2437).

4. The antibody according to claim 1 which is associated with at least one of a solid phase and a reporter system component.

5. An in vitro or in vivo diagnostic agent comprising the antibody according to claim 1.

6. A test kit comprising at least one antibody according to claim 1.

7. A process for preparing the antibody according to claim 1 comprising the step of immunizing a host with one or more oligopeptide comprising the amino acid sequence SEQ ID NO: 4.

8. The process according to claim 7, wherein said oligopeptide is a carrier-bound oligopeptide.

9. An animal cell, plant cell, prokaryotic cell, or isolated human cell which produces the antibody according to claim 1.

10. The cell according to claim 9, wherein said cell is a hybridoma cell line.

11. The cell according to claim 10, wherein the hybridoma cell line is named 98-31/04 and was deposited with the DSMZ under accession number DSM ACC2437.

* * * * *

SEQUENCE LISTING

```
<160> NUMBER OF SEQ ID NOS:  4

<210> SEQ ID NO 1
<211> LENGTH: 6
<212> TYPE: PRT
<213> ORGANISM: Homo sapiens

<400> SEQUENCE: 1

Arg Ser Lys Arg Cys Gly
 1               5

<210> SEQ ID NO 2
<211> LENGTH: 12
<212> TYPE: PRT
<213> ORGANISM: Homo sapiens

<400> SEQUENCE: 2

Asp Ser Pro Arg Ser Lys Arg Cys Gly Asn Leu Ser
 1               5                  10

<210> SEQ ID NO 3
<211> LENGTH: 6
<212> TYPE: PRT
<213> ORGANISM: Homo sapiens

<400> SEQUENCE: 3

Pro Gly Lys Lys Arg Asp
 1               5

<210> SEQ ID NO 4
<211> LENGTH: 12
<212> TYPE: PRT
<213> ORGANISM: Homo sapiens
```

```
<400> SEQUENCE: 4

Val Gly Ala Pro Gly Lys Lys Arg Asp Met Ser Ser
 1               5                  10
```